United States Patent [19]

Anderson et al.

[11] Patent Number: 5,035,901
[45] Date of Patent: Jul. 30, 1991

[54] BONE INDUCING AGENT FROM A HUMAN OSTEOSARCOMA CELL LINE

[75] Inventors: H. Clarke Anderson, Shawnee Mission, Kans.; Kazuomi Sugamoto, Oyodoku Osaka, Japan

[73] Assignee: University of Kansas, Kansas City, Kans.

[21] Appl. No.: 107,299

[22] Filed: Oct. 9, 1987

[51] Int. Cl.$^5$ .................... A61K 35/12; C12N 5/08
[52] U.S. Cl. .................... 424/573; 435/240.2
[58] Field of Search .................... 435/259, 68, 240.2; 424/195.1, 95, 573; 530/828, 422

[56] References Cited

U.S. PATENT DOCUMENTS

| | | | |
|---|---|---|---|
| 4,160,018 | 7/1979 | Bjorklünd | 424/95 |
| 4,294,753 | 10/1981 | Urist | 530/840 |
| 4,544,552 | 10/1985 | Fraefel et al. | 435/240.1 |
| 4,752,578 | 6/1988 | Moore et al. | 435/226 |
| 4,761,471 | 8/1988 | Urist | 530/840 |

OTHER PUBLICATIONS

Takaoka et al., Biomed. Res., 2(5), 466–471, 1981.
Rodan et al., Cancer Res., 47, 4961–4966, 9-15-87.
Fogh et al., p. 120, in *Human Tumor Cells in Vitro*; J. Fogh, ed. Plenum Press, N.Y. 1975.
Amitani, K. et al., "Osteoinduction by cell free material from murine osteosarcoma and its cultured cell line" Gann, 66:327–329 (1975).
Anderson et al., "Formation of tumors containing bone after intramuscular injection of transformed human amnion cells (FL) into cortisone–treated mice", Am. J. Path., 44:507–519 (1964).
Anderson and Coulter, "Bone inducing capability of cultured human cells (FL) and Hela compared to that of various types of injury" Fed. Proc., 27:475 (1968).
Anderson, "Epithelial–mesenchyrmal cell interactions" Clin. Orthop., 119:211–224.

*Primary Examiner*—Jacqueline Stone
*Attorney, Agent, or Firm*—Felfe & Lynch

[57] ABSTRACT

Human osteosarcoma Saos-2 cell extracts as for example in the form of a killed-cell, defatted cell residue are found to retain bone inducing-agent(s) after freeze-drying. Pellets of this material were found to promote new bone formation. This material is useful therefore for healing bone defects, bone tumors, bone fractures and in promoting bone graft assimilation.

3 Claims, No Drawings

BONE INDUCING AGENT FROM A HUMAN OSTEOSARCOMA CELL LINE

SUMMARY

The invention concerns production of a bone-inducing agent (BIA) from a human osteosarcoma cell line (Saos-2).

DESCRIPTION

It has been known for a long time that devitalized and decalcified mammalian bone contains bone morphogenetic factor(s), commonly referred to in the art as bone morphogenetic protein (BMP), with the ability not only to stimulate proliferation of preosseous mesenchymal cells of skeletal muscle, but also to promote their differentiation into ectopic new cartilage, bone and bone marrow (Urist, M. R. (1965) Science 150:893; Van de Putte, K. A., et al. (1965) Clin. Orthop. and Rel. Res. 43:257).

A bone-inducing agent (BIA) appears to exist in certain strains of transformed human epithelial cells carried in culture, including FL transformed amnion cells (Anderson, H. C., et al. in (1964) Am. J. Path. 44:507-519 and in (1967) J. Cell. Biol. 33:165-177), HeLa cells (Anderson, H. C. et al. (1968) Fed. Proc. 27:475), WISH amnion cells (Wlodarski, K. (1969) Exp. Cell Res. 57:446-448), and other cell lines (such as neoplastic cells) (Wlodarski, K., et al. (1971) Calcif. Tiss. Res. 7:345-352; Wlodarski, K. (1985) Clin. Orthop. and Rel. Res. 200:248-265), in Dunn mouse osteosarcoma cells of the BFO strain (Amitani, K., et al. (1975) Gann 66:327-329; Hanamura, H. Y., et al. (1980) Clin. Orthop. and Rel. Res. 148:281-290; Takaoka, K., et al. (1980) Clin. Orthop. and Rel. Res. 148:274-280) and in Nagusa cultured human osteosarcoma cells wherein a brief Abstract indicates these cells supposedly can be devitalized and implanted as pellets with retention of BMP activity (Takaoka, K., et al. (1986) 1st International Workshop on Cells and cytokines in Bone and Cartilage). However the Nagusa cells are not available and therefore this finding cannot be confirmed.

A large body of literature describes methods to extract, purify and bioassay the extracted BMP from decalcified bone and from the BF osteosarcoma cell line (Urist, M. R., et al. (1979) Proc. Nat. Acad. Sci. (USA) 76:1828-1832; Takaoka, K., et al. (1982) Clin. Orthop and Rel. Res. 164:265-270; Yoshikawa, H., et al. (1982) Clin. Orthop. and Rel. Res. 163:248-253; Yoshikawa, H., et al. (1984) Clin. Orthop. and Rel. Res. 182:231-235). Also see patents to Urist et al. U.S. Pat. Nos. 4,455,256, 4,619,989 and 4,294,753 which involve demineralizing bone tissue to obtain BMP which appears to be a protein (U.S. Pat. Nos. 4,596,574 and 4,525,909). There is also a European patent application No. 86 110 935 13 to Urist concerning bone peptides. Delivery systems in the art appear to involve use of several different carrier materials, see U.S. Pat. Nos. 4,596,574, 4,526,909, 4,394,370, 4,563,489, 4,472,840, 4,563,350. However extraction of a bioactive bone-inducing agent has never been described from FL, WISH, HeLa, KB or other human transformed epithelial or other cells which are routinely carried in culture and commonly available.

Unexpected recent experimental results have led to the discovery of a bone-inducing agent residing within a strain of human osteosarcoma cells officially designated Saos-2 (ATCC No. HTB 85). The Saos-2 is an established epithelial-like human osteosarcoma tumor cell line initially isolated and characterized by Fogh and Trempe that does not form tumors when grown in nude mice (Fogh, J., et al. (1975) In: Human Tumor Cells In Vitro J. Fogh, Ed. Plenum Press, N.Y. pp 115-159). Although the Saos-2 cells have been extensively used and characterized since their establishment more than 10 years ago, until now the cell line's bone-inducing ability was unknown.

It is notable that the bone-inducing activity contained in the Saos-2 cells does not depend upon the Saos cell being in a living state, as is the case with bone-induction by FL, HeLa, WISH and KB cells (Wlodarski, K. (1985) Clin. Orthop. and Rel. Res. 200:248-265; Anderson, H. C. (1976) Clin. Orthop. and Rel. Res. 119:211-224), but the BIA in Saos cells is retained in a freeze-dried, defatted, killed-cell residue. This means that the BIA of Saos can be extracted, concentrated, purified and bioassayed using already described techniques (Amitani, K., et al. (1975) Gann 66:327-329; Hanamura, H. Y., et al. (1980) Clin. Orthop. and Rel. Res. 148:281-290; Takaoka, K., et al. (1980) Clin. Orthop. and Rel. Res. 148:274-280; Takaoka, K., et al. (1986) 1st International Workshop on Cells and cytokines in Bone and Cartilage; Urist, M. R., et al. (1979) Proc. Nat. Acad. Sci. (USA) 76:1828-1832; Takaoka, K., et al. (1982) Clin. Orthop and Rel. Res. 164:265-270; Yoshikawa, H., et al. (1982) Clin. Orthop. and Rel. Res. 163:248-253; Yoshikawa, H., et al. (1984) Clin. Orthop. and Rel. Res. 182:231-235).

The strain of Saos-2 cells tested was obtained as a gift from the laboratory of Dr. Michael Whyte, Jewish Hospital, St. Louis, Mo. This cell line is grown routinely as a monolayer in glass or plastic tissue culture vessels in Dulbecco's minimal essential medium (DMEM) containing 10% fetal calf serum (FCS) and in an atmosphere of 5% $CO_2$ in air at 37° C. Samples of these Saos-2 (also known as Saos-2 BIA) cells as grown in our laboratory are on deposit at the ATCC as of 9/30/87 under designation CRL - 9559, ATCC is the American Type Culture Collection located at 12301 Parklawn Drive, Rockville, Md. 20852.

Bone-inducing pellets of these freeze-thawed, defatted Saos cells are prepared by 1) growing Saos cells to confluence in large prescription bottles; 2) removal of the cells by scraping; 3) washing of the cells two times in serum-free phosphate-buffered salt solution (PBS); 4) centrifuging 20 to $25 \times 10^6$ cells in a conical centrifuge tube to form a condensed pellet; 5) defatting and devitalizing with 100% acetone; and 6) freeze-drying for preservation.

Pellets are implanted beneath the fascia of the shoulder, adjacent to muscle in either: a) ether-anaesthetized nude mice or b) ether-anaesthetized weanling mice given a weekly abdominal subcutaneous injection of 5 mg of cortisone acetate suspension prior to pellet implantation. Non-bone inducing "control" pellets are made from $20-25 \times 10^6$ UMR-106 rat-osteosarcoma cells derived from radiation-induced osteosarcoma by the procedures described above, and implanted as above.

After three weeks on standard lab chow and water ad libitum the mice are sacrificed by cervical dislocation, and the implantation sites are dissected out and processed by routine histological procedures to yield non-decalcified, hematoxylin and eosin-stained sections. The sections are examined microscopically and graded for the presence of bone, cartilage and bone marrow. The results of pellet implantation are given below in Table I.

TABLE I

| Bone-inducing activity of intramuscularly implanted pellets of devitalized Saos-2 human osteosarcoma cells versus pellets of UMR-106 rat osteosarcoma cells after three weeks in nude mice ||||
| CELL TYPE | N | CARTILAGE | BONE | MARROW |
| --- | --- | --- | --- | --- |
| Saos-2 | 16 | 100% | 100% | 100% |
| UMR-106 | 9 | 0% | 0% | 0% |

There are several advantages in being able to obtain a bone-inducing agent(s) from a human cell line that is permanently adapted to growth in cell culture (i.e. an "immortalized" cell line) including:

1. The ability to grow large quantities of producer cells by mass culture techniques for large scale therapeutic and other utilization;

2. The fact that the BIA produced in Saos cells is of human origin, and thus will be less likely to produce untoward reactions in human recipients. Thus new bone will be created and formed by host cells attracting a host blood supply and this formation will not be rejected by host immune mechanisms since it is host-like in nature.

3. The Saos cells are devitalized prior to use by methods which destroy any malignant potential or any known infectious or carcinogenic agents. However it is known that even living Saos cells do not form tumors in nude mice (Fogh, J. (1985) supra), and our experiments confirm that live Saos-2 cells will not grow in nude mice and did not induce bone in all 8 implants tested to date.

4. Growing a producer cell line of "epithelial-like" cells such as Saos that does not synthesize or secrete a significant amount of matrix, can eliminate most contaminating extracellular maxtrix from the starting material. The presence of matrix may impede extraction of the bone-inducing substance.

5. The availability of a permanently growing, BIA-producing cell line can provide a good source of the specific m-RNA coding for BIA. The latter then can be used to produce a BIA c-DNA by well-established technology. The BIA c-DNA can be sequenced to determine the primary structure of BIA. Ultimately cloning of the gene for BIA will facilitate development of an in vitro production method that utilizes transduced E. coli to synthesize BIA.

If BIA in its extracted form is soluble in aqueous solution and therefore may not remain localized in vivo sufficiently long at the site of desired new bone formation due to its rapid dissolution into the extracellular fluid, insoluble or slowly biodegradable carrier materials can be used to retain BIA at the site of desired action by methods known in the art for a sufficient time to allow bone-induction to take place.

To augment fracture healing and the repair of bony defects by BIA, this material can be applied directly to such fractures and bony defects with or without a suitable carrier. Studies have been reported indicating that crude, decalcified bone powder, as a source of BMP, can speed the healing of experimentally induced bone defects (Einhorn, T. A., et al. (1987) J. Bone Jt. Surg. 66A:274–279; Gendler, E. (1986) J. Biomed. M. R. 20:687–697; Glowacki, J., et al. (1981) Calcif. Tiss. Intern. 33:71–76; Kaban, L. et al. (1982) J. Oral. Maxillofac. Surg. 40:623–626; Nilsson, O. et al. (1985) Clin. Orthop. and Rel. Res. 195:275–281; Sato, K. et al. (1985) Clin. Orthop. and Rel. Res. 197:301–311; Upton, J., et al. (1984) J. Hand Surg. 9A:388–391; Urist, M. R., et al. (1987) Clin. Orthop. and Rel. Res. 214:295–304; Vandersteenhaven, J. J., et al. (1983) J. Biomed. M. R. 17:793–806).

The range of situations in which BIA-speeded bone repair can be useful is almost limitless, e.g. 1) replacement of bone removed for tumor surgery, for maxillofacial repair, etc.; 2) to speed the rigid fusion of vertebral bodies in spinal surgery for slipped disc, scoliosis, etc.; 3) when incorporated into a suitable carrier, BIA as a bone-grafting material in the varied clinical situations when bone grafting is necessary; 4) to speed the healing of traumatic fractures after open reduction in young active individuals, and in slowly healing fractures of the hip in the elderly; 5) to augment the bonding of resected bone surfaces to porous biocompatible prostheses; 6) to effect the repair of non-union fractures; etc.

Purified or semi-purified BIA from Saos-2 cells can also be used to develop monoclonal and/or polyclonal antibodies to BIA. Once a neutralizing antibody is obtained, or once a purified-active BIA can be used as antigen, then the reagents will be at hand to develop a simple and rapid immunoassay for the presence of BIA.

It is then possible to apply the immunoassay and/or anti-BIA antibody to several tasks including: 1) rapid analysis of the content of BIA in a variety of natural materials to determine whether natural sources of bone promoting materials exist other than Saos type cells or decalcified bone; 2) as a diagnostic test to immunoassay circulating BIA in patients who may exhibit abnormal serum levels of BIA, e.g. in osteosarcoma, in metastic or recurrent osteosarcoma, in Paget's disease of bone, in osteoporosis (where levels of BIA may be reduced), in parathyroid induced bone disease, and in other metabolic diseases affecting bone turnover such as diabetes and hyperthyroidism; 3) to develop experimental reagents to immunolocalize BIA in various organs and in their cells, cytoplasm and/or nuclei, e.g. as an antibody probe, it can help to analyse and possibly augment the mechanism of bone-induced action of BIA; 4) to use anti-BIA as a screening reagent during the isolation and cloning of the gene for BIA as a necessary step in sequencing and synthesizing BIA or BIA analogues; 5) anti-BIA or subunits of the antibody may be used for diagnostic imaging when coupled with a suitable radioisotopic tag to disclose occult bone tumors or sites of increased bone turnover where BIA is being synthesized in vivo; 6) anti-BIA or subunits thereof can be used for therapy of bone tumors when coupled with a radiolabel or cytotoxic agent.

Diagnostic imaging of bone tumors or localized areas of fracture or increased bone metabolism (as in Paget's disease) might be accomplished if anti-BIA or functional subunits of the antibody could be conjugated with a radioactive tag such as $^{131}$Iodine or $^{111}$Indium. Such diagnostic reagents have been reported successful for radionuclide imaging of human bone and/or osteosarcomas (Armitage, et al., (1986) Cancer 58:37–42) using a monoclonal antibody raised against a human osteosarcoma cell line (791 T/36) whole cell antigen. In this study which showed improved imaging over the conventional TC99-diphosphonate method, the monoclonal antibody was only selective for bone but also cross-reacted against colon, lung, prostate and cervical (HeLa) carcinoma cells. A bone specific anti-BIA such as described here would presumably do a much better job of targeting. Upon injection of tagged anti-bone BIA antibody into the patient or animal, the antibody should accumulate at bone sites for example of elevated bone synthesis, storage and/or release and could be used for radionuclide imaging.

An antibody to BIA might also be conjugated with a tumoricidal agent for in vivo chemotherapeutic homing in bone cancers. Targeted monoclonal antibodies carrying cytotoxic agents such as ricin A-chain, pseudomonas exotoxin-A or methotrexate or $^{131}$Iodine are being actively investigated for treatment of malignant lymphoma (Bregni et al., Cancer Res. (1986) 46:1208–1213) breast cancer (Bjorn, M. J. (1986) Cancer Res. 46:3262–3267), colorectal cancer, (Oldham, R. K. (1984) Med. Oncol. Tumor Pharmacother. 1:51–62) and other types.

Pure or semi-pure BIA or anti-BIA can be useful in the diagnosis or treatment of veterinary diseases and neoplasms. For example, the repair of fractures in horses is often quite slow because of the large fracture size and displacement of bone fragments, but would be materially assisted by splinting and/or bone replacement by biodegradable material(s) carrying BIA. Another possible use would be in the repair of deviated front legs (valgus deformity) which is frequent in large dogs. These deformities are usually treated by therapeutic fracture, wedge grafting and fusion. Healing and fusion would be speeded by grafted material containing BIA. Similarly fusion of the spine in disc surgery and broken backs of dogs, particularly dachshunds, could be promoted by implanted BIA. Finally, the diagnosis of osteosarcoma, which occurs often in the distal radius of large breeds of dogs, would be facilitated by a serum ELISA test for increased circulating BIA.

Purified human BIA or an active subunit thereof can be used for systemic treatment to augment bone growth, to prevent bone loss in metabolic disease such as osteoporosis, or to speed fracture healing and bone replacement and repair through systemic administration. Thus the invention is not limited to the specific examples shown but it is understood the specification and examples serve as illustrations of the present invention and that other embodiments and equivalents within the spirit and scope of the invention will suggest themselves to those skilled in the art.

What is claimed:

1. Method for inducing bone formation in a mammal which comprises treating a mammal in need of bone formation or healing with an amount of devitalized, freeze dried Saos-2 cells sufficient to promote bone healing or bone formation.

2. Method of claim 1, wherein said Saos-2 cells are defatted Saos-2 cells.

3. Method of claim 1, wherein said mammal is in need of healing of a bone defect, treatment of a bone tumor or of promotion of assimilation of a bone graft.

* * * * *